(12) United States Patent
Adiga et al.

(10) Patent No.: US 7,326,382 B2
(45) Date of Patent: Feb. 5, 2008

(54) APPARATUS AND METHOD FOR FINE MIST STERILIZATION OR SANITATION USING A BIOCIDE

(75) Inventors: Kayyani C. Adiga, Macon, GA (US); Rajani Adiga, Macon, GA (US)

(73) Assignee: Nanomist Systems, LLC, Warner Robins, GA (US)

( * ) Notice: Subject to any disclaimer, the term of this patent is extended or adjusted under 35 U.S.C. 154(b) by 812 days.

(21) Appl. No.: 10/393,224

(22) Filed: Mar. 20, 2003

(65) Prior Publication Data

US 2004/0005240 A1    Jan. 8, 2004

Related U.S. Application Data

(60) Provisional application No. 60/365,870, filed on Mar. 20, 2002.

(51) Int. Cl.
*A61L 2/22* (2006.01)
(52) U.S. Cl. ............... 422/28; 422/37; 977/773
(58) Field of Classification Search .......... 422/29, 422/28, 37; 977/700, 773
See application file for complete search history.

(56) References Cited

U.S. PATENT DOCUMENTS

| | | | |
|---|---|---|---|
| 3,723,060 A | 3/1973 | Lisiecki | |
| 4,296,068 A | 10/1981 | Hoshino | |
| 4,366,125 A | 12/1982 | Kodera et al. | |
| 4,541,986 A | 9/1985 | Schwab et al. | |
| 4,680,163 A | 7/1987 | Blidschun et al. | |
| 4,797,255 A | 1/1989 | Hatanaka et al. | |
| 4,844,874 A | 7/1989 | deVries | |
| 4,863,688 A | 9/1989 | Schmidt et al. | |
| 4,919,159 A | 4/1990 | Forrest et al. | |
| 5,445,792 A | 8/1995 | Rickloff et al. | |
| 5,595,713 A | 1/1997 | Gohara et al. | |
| 5,902,619 A | 5/1999 | Rubow et al. | |
| 5,904,901 A | 5/1999 | Shimono et al. | |
| 6,277,344 B1 | 8/2001 | Hei et al. | |
| 2003/0007916 A1 | 1/2003 | Khorzad | |
| 2003/0035754 A1* | 2/2003 | Sias et al. | ............ 422/29 |

FOREIGN PATENT DOCUMENTS

| | | |
|---|---|---|
| GB | 2089213 A | 6/1982 |
| WO | WO 99/66961 A1 | 12/1999 |

* cited by examiner

*Primary Examiner*—Gladys J P Corcoran
*Assistant Examiner*—Sean E. Conley
(74) *Attorney, Agent, or Firm*—Brian D. Bellamy

(57) ABSTRACT

A method of sterilizing a site or contained volume includes providing an aqueous biocide solution containing a biocide agent such as hydrogen peroxide. A mist of reactive biocide droplets is generated by atomization at ambient pressure from the biocide solution and a flow of carrier medium or air is provided in communication with the mist. The flow of carrier medium is controlled to generate a biocide mist comprising a concentration of stable mist droplets within the carrier medium. By controlling aersolization, extraction and delivery of the stable mist droplets, a sufficient portion of the stable mist droplets for a sterilizing treatment of a designated site do not coalesce prior to treatment interaction with the treatment site. The process of formation, stabilization and extraction are done in-situ so that droplets do not coalesce during transport.

18 Claims, 5 Drawing Sheets

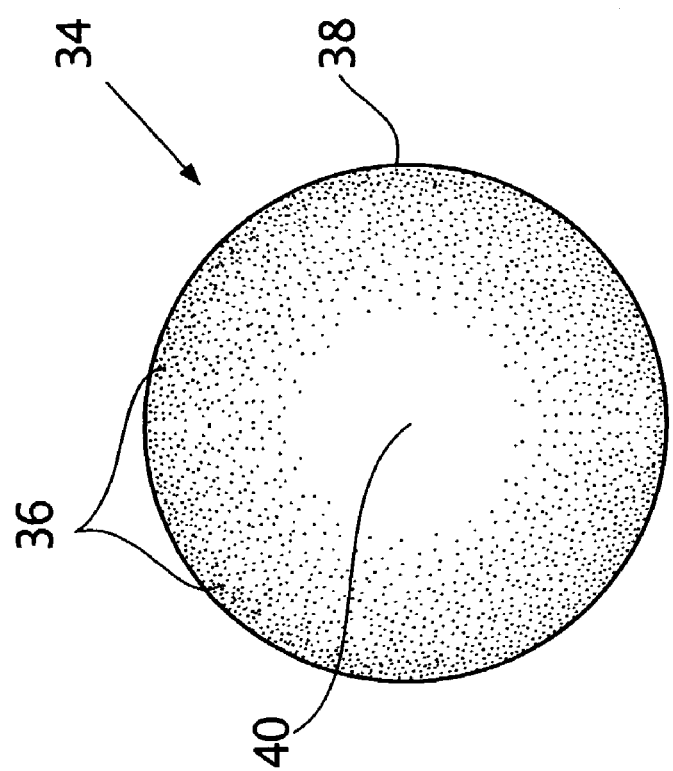
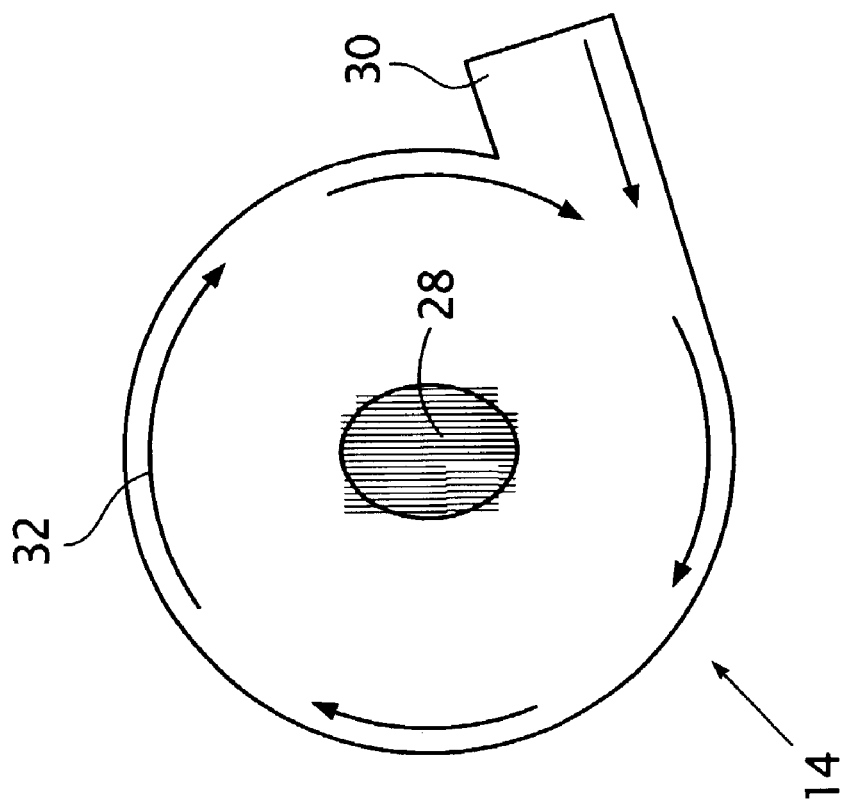

APPARATUS AND METHOD FOR FINE MIST STERILIZATION OR SANITATION USING A BIOCIDE

PRIORITY CLAIM

The present application claims priority of U.S. provisional patent application No. 60/365,870 filed on Mar. 20, 2002.

BACKGROUND OF THE INVENTION

1. Field of the Invention

The present invention relates to sterilization or sanitation of a surface or volume, especially a room or building, using a sterilizing mist. In particular, the invention pertains to using a sterilizing mist delivered at ambient pressure and having droplets generally less than 10 micron, preferably less than a micron and of sufficient throughput and reactivity to be effective in the elimination of bacteria using various concentrations of a biocide such as hydrogen peroxide solution. The methodology provides for extraction and delivery of a stable sterilizing mist dispersed in gas-like manner for treatment of items, space or surfaces in a volume.

2. Description of the Prior Art

As demonstrated by the ongoing efforts beginning in November 2001 to decontaminate federal buildings of anthrax, a continuing need exists for improved methods for sanitizing items and areas like those found within buildings and dwellings. Anthrax poses a specific danger in that these instances in the year 2001 involved anthrax spores that were delivered in sealed envelopes and that leached or became airborne and contaminated surfaces and spaces. Ultimately, chlorine dioxide gas had to be used to decontaminate the federal buildings involved. This prior method of using chlorine dioxide gas came at great expense because of the toxic hazards of chlorine dioxide gas to humans and because of the damage chlorine dioxide gas causes to documents and other items within the area treated. An equally effective, yet safer and less obtrusive, alternative would have been preferred if available.

Other general methods of sterilization and bacteria eradication have usually included heating, autoclaving, retorting, and pasteurization. Chemical methods used in the past have included gas or vapor sterilization using ethylene oxide or hydrogen peroxide vapor, and the low temperature gas plasma, STERRAD. Further, chemicals have been commonly used in the form of liquids, gels, and stored pressure aerosols for application to surface areas. Various forms of gamma, electron-beam, x-ray, and ultraviolet radiation have been used in sterilization, and filter sterilization is sometimes used.

Because of it strong oxidizing power, hydrogen peroxide acts as a sterilizing agent, but has not been used successfully for sterilizing surfaces and areas like those within buildings and dwellings. Hydrogen peroxide in gasified vapor phase is known to be unstable and decomposes to water and oxygen. Otherwise, sterilizing an area by providing hydrogen peroxide in gasified vapor phase could have been considered. However, because of its instability in the gas phase, vaporized hydrogen peroxide is inefficient for use in sterilization. With hot air flow assisted gasification/vaporization, considerable decomposition of hydrogen peroxide into H2O (water) and oxygen occurs very rapidly. The pre-decomposition of the hydrogen peroxide before reaching the bacterial site or intended surface is of great disadvantage because it decreases the reactivity and effectiveness of the agent in achieving the desired killing power because less reactive oxygen will contact the bacterial site.

Further, known methods that are effective in using hydrogen peroxide as a sterilizing agent have not been conducive to use for sterilizing articles using a hydrogen peroxide agent alone or in sterilizing items and surfaces in larger areas such as rooms in buildings and dwellings. For instance, recent gas plasma approaches using hydrogen peroxide are limited to fixed volume applications such as to sterilize surgery equipment or items in specially designed cabinets of only several liters in volume. Other approaches have not permitted a sufficient exposure to the hydrogen peroxide agent to be effective for sterilization without it being coupled with a secondary sterilizing mechanism.

U.S. Pat. No. 4,680,163 to Blidschun et al. teaches a process and apparatus for sterilizing open-topped containers in which a sterilizing agent such as hydrogen peroxide is ultrasonically atomized into electrically charged droplets to be deposited on the inner surfaces of a container. As described by Blidschun, the hydrogen peroxide droplets produced using ultrasonic atomization are in the range of 2-4 μm. Blidschun teaches that the use of an electrostatic field is necessary to convey the droplets to the surface of the container to be sterilized in a shorter time. The use of electrostatic charging provides sufficient rate of deposition of droplets to sterilize the container surface before the atomic oxygen formed by H2O2 decomposition recombines to form an oxygen molecule. However, using electrostatic charge to speed deposition of droplets is not practical or viable for sterilizing unpredictable and/or physically complex surfaces or articles and areas of larger volume such as encountered when entire rooms or buildings must be sterilized. Thus, Blidschun does not teach a methodology utilizing hydrogen peroxide as a sterilizing agent that would be applicable to the need for an improved method for sanitizing a variety of articles and surfaces in areas in large volumes such as buildings and dwellings, where items or surfaces cannot be readily sterilized using a wet aseptic process or charged electrostatically.

U.S. Pat. No. 4,366,125 to Kodera et al. teaches the use of ultrasonically atomized hydrogen peroxide mist of about 10 μm in diameter as a sterilizing agent that is very weak but is effective when used in a combination of steps including ultraviolet radiation. Following the teaching of Kodera would suggest that ultrasonically atomized hydrogen peroxide in mist form could not be effective in decontaminating articles and surfaces in a room or building. As in Blidschun discussed above, Kodera suggests that H2O2 mist on scale of several microns or more as described would decompose and the atomic oxygen recombine to form an oxygen molecule before effective sterilization by the hydrogen peroxide mist could take place. Thus, producing a stable mist effective for sterilization has been very difficult and elusive in the prior art.

Moreover, it has been found, as suggested by Blidschun and Kodera, that the ultrasonic method of producing a sterilizing mist has serious limitations. In particular, scaling a sterilizing mist to larger throughputs makes accomplishing efficient aerosolization to make a stable mist very difficult. The mist droplets revert and coalesce to form water, thereby reducing throughput of sterilizing mist product drastically and making the mist insufficient for sterilizing. Likewise, prior art does not discuss or provide methodology that would achieve throughputs beyond about 50 ml/min of mist. Heretofore, methods to extract and deliver such levels of mist throughput have been unavailable.

In summary, a method of using hydrogen peroxide in a stable gas-like phase that would be effective for sterilizing an area has been unavailable and infeasible. Known methods of using hydrogen peroxide in a mist form did not provide sufficient throughput, production quality of mist, and mass flow to merit consideration for use in a gas-like mist for volume application in sanitizing articles and surfaces in areas such as rooms, buildings, or air ducts. Therefore, as illustrated by the discussion of prior art, hydrogen peroxide mist previously has been used only in wet aseptic processes rather than in volume applications utilizing hydrogen peroxide in any gas or gas-like form.

Thus, a method is needed of producing a mist using ultrasonic atomization, in-situ aerosolization, and extraction processes to scale, transport and disperse the sterilizing mist to a volume whereby throughput, production quality and mass flow of the mist are controlled and suitable for volume fumigation and sterilization.

SUMMARY OF THE INVENTION

The invention provides a method of producing a sterilizing mist that is effective in sterilizing a volume and it's contents within a room or building. The mist is generated at ambient pressure using electronic ultrasonic transducers to convert electrical frequency input into mechanical ultrasonic vibrations. The mist throughput is scalable using variations of frequency and oscillator surface area, and delivery devices may be designed for application by hand to small areas, to medium scale applications suitable for devices designed to be carried by backpack, or for large scale applications delivered to entire rooms or buildings.

The quality of the mist is maintained by using sufficient frequency and conditions to produce a plume of mist having a high number of extremely fine droplets concentrated about the exterior portions of the plume. The invention provides for primarily extremely fine droplets to be extracted from the plume using a swirling flow of carrier gas that is applied tangential to the extraction column to entrain only the smaller droplets. The larger droplets are left in the center of the plume to fall back into the reservoir of solution as a fountain of water. The unique tangential related flow of carrier medium and the in-situ extraction column markedly improves throughput of mist.

The sterilizing mist is delivered having very low momentum wherein the flow of mist and carrier gas is nearly a free convection flow. The low momentum provides enhanced mist stability whereby the mist is dispersed without coalescing because of low kinetic energy created by the motion of the mist droplets. The throughput and stability of mist droplets provided by the methodology produce sterilizing mist droplets that diffuse with a concentration gradient effective in sterilizing volumes of space and contents using a sterilizing mist of hydrogen peroxide solution or other biocide solution. Further, the extremely fine droplet size of the mist is maintained and controlled after the mist is produced and as the mist is delivered, which is necessary for diffusing the mist at the effective concentration gradient discussed.

A mist produced from a three percent solution of hydrogen peroxide is highly efficient for sterilizing an area due to dramatic gains in reactivity and improved flow behavior provided by a high number of nanoscale size droplets of less than one micron. In particular, droplets in the size range less than 10 micron have been found to be very effective.

The large surface area of mist provided by the large number of small droplets provides for increases in reactivity related directly to the increased reactive surface area. If nanoscale droplets are used, droplets provide an additional dynamic not found in larger scale droplets. The molecules within the droplets tend to become very surface concentrated, such that 80 to 90 percent of the reactive molecules are near the surface of the droplet and contribute to enhanced reactivity. Therefore, the mist is highly reactive and highly effective in sterilization applications.

The mist of extremely small droplets exhibit improved flow that makes the mist suitable for sterilizing areas such as rooms and buildings. The mist flows very much like a gas to sterilize nooks and corners of small and large-scale rooms without being obstructed by physical objects in the path of the mist.

BRIEF DESCRIPTION OF THE DRAWINGS

FIG. 4 is a schematic cross-section illustration of a column of generated mist depicting the tangential flow extraction of fine mist droplets.

FIG. 5 is a cross-section view of a mist droplet of the scale introduced by an embodiment of the invention for fine mist sterilization.

DETAILED DESCRIPTION OF THE INVENTION

Figure 1:
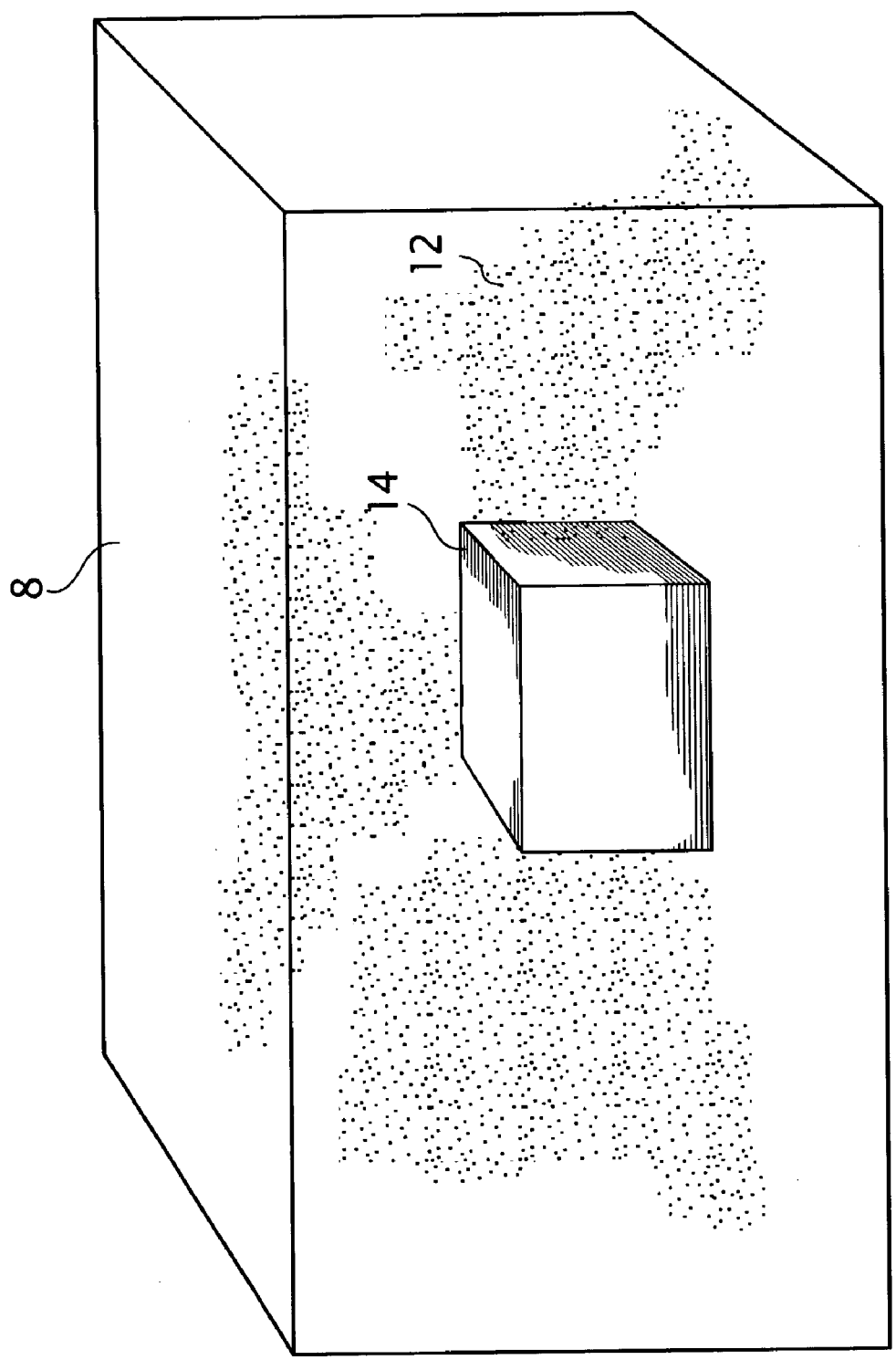
FIG. 1 is a schematic illustration of a first embodiment of the invention for the treatment of a volume of space using a fine-mist generating device.

The present invention uses an aqueous biocide solution 10 comprised of a biocide agent and solvent, particularly hydrogen peroxide solution, to generate a mist for application in sterilizing an environment. An example of an embodiment of the invention is shown in FIG. 1 in which a mist 12 is generated from a device 14 for sterilizing an enclosed environment 8, such as a room or building. The hydrogen peroxide is stabilized in low concentrations such as in solutions containing 3% by weight hydrogen peroxide in water. The actual concentration of hydrogen peroxide in the solution does not have to be 3% wt in water, but may be more or less depending upon the desired concentration of the solution. In fact, an advantage of the present invention is that enhanced reactivity promotes the conservation of hydrogen peroxide consumed during application. In general, the combination of the variables of concentration of solution and time of exposure will provide a formula for determining the desired sanitizing power. Thus, changing the concentration of the hydrogen peroxide or other biocide solution may vary the efficiency of the agent.

Figure 2:
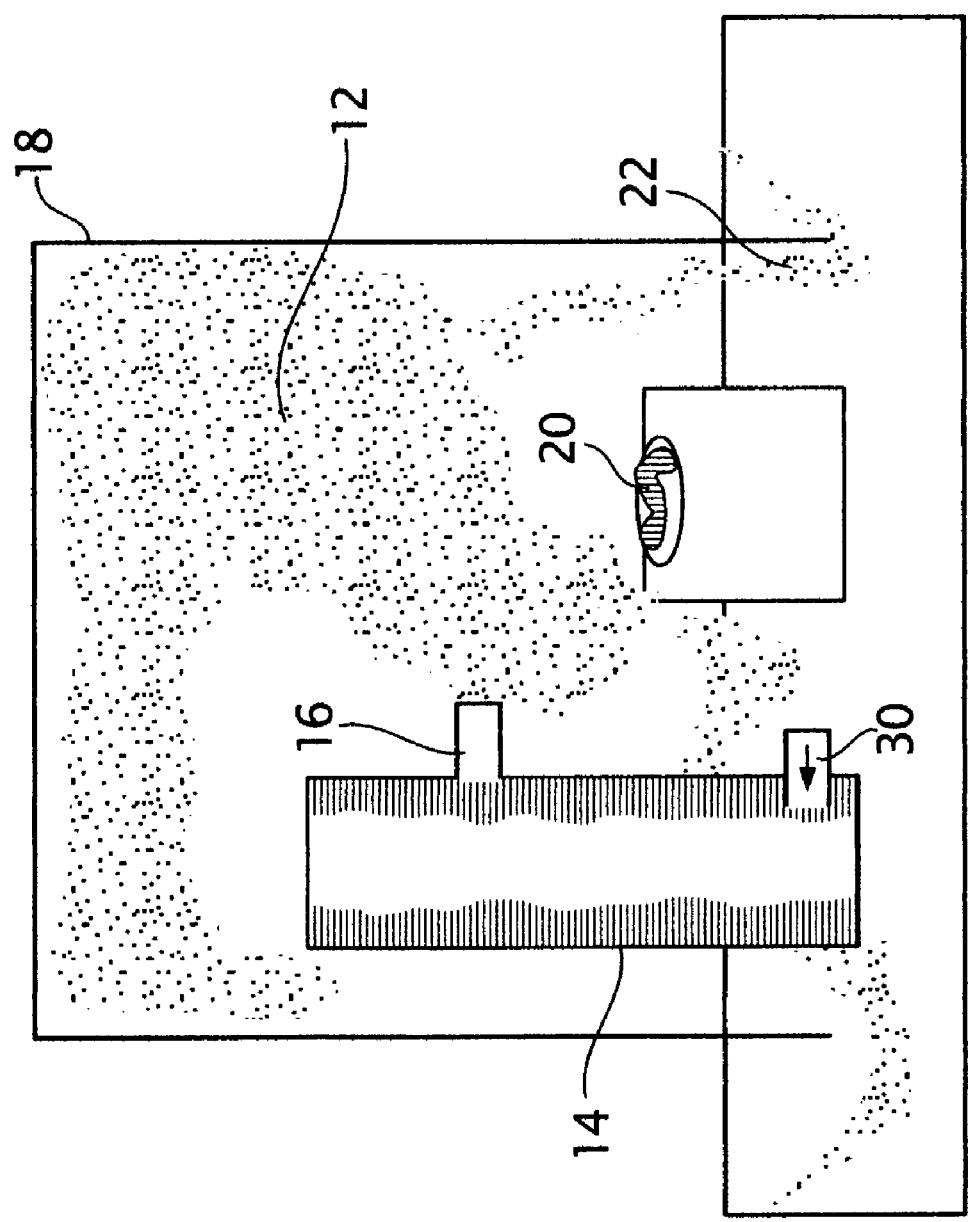
FIG. 2 is a schematic plan illustration of an experimental volume of space with a mist applied therein to kill bacterial spores on a surface.

Applying concepts from the invention, the effectiveness of hydrogen peroxide mist 12 in killing bacteria was verified by providing a hydrogen peroxide mist of 3% weight and using a small-scale mist generator 14 with outlet 16 placed inside an inverted container 18 as shown in FIG. 2. The mist was tested to kill the bacteria *Bacillus subtilis* HB, depicted by the bacterial spore 20. A natural leak 22 at the base of the container represented a room with reasonably secured ventilation outlets but with cracks and natural leaks inherent in most infrastructures. While, varying the time intervals of exposure and providing a flow rate of about 1 gram/minute, only some residual bacteria spores remained after 10 minutes of treatment, and the spores were completely killed by 20 minutes of exposure to the mist.

While concentration is one aspect of the invention considered, exposure of the target to the hydrogen peroxide agent is another aspect that is important to killing bacteria and sanitization. Providing mist throughput from the generating unit 14 that is capable of delivering the mist 12 to the area to be treated promotes such exposure. The throughput of the device and methods described herein is variable from a few ml/min to a few liter/min, and, therefore, scalable to a variety of applications, whereby sufficient mist throughput is provided according to the scale of the treatment area.

A piezoelectric transducer 24 connected to a power supply 26 generates the sterilizing mist 12 from the biocide solution 10 contained in a reservoir at ambient pressure and at ambient temperature. The reservoir is contained within the chamber walls 50 of the device 14, and the walls are preferably cylindrical as depicted in FIGS. 2-4. The piezoelectric transducer 24 is submerged in a bath of solution or arranged in physical communication with the solution. If the biocide solution is corrosive or is a chemical hostile to the transducer or other elements of the mist-generating device, the biocide solution may be placed in a sound transparent container, and the container placed on water-bed in which the transducer is immersed. This will avoid direct contact of biocide solution with the transducer elements.

Figure 3A:
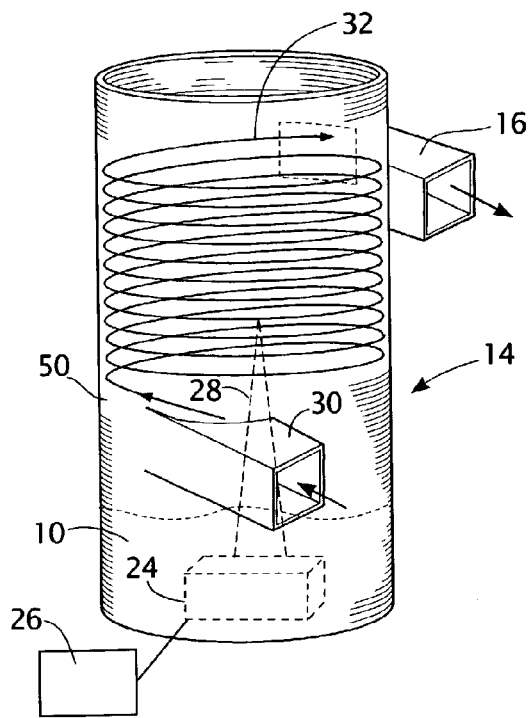
FIG. 3a is a perspective view of one embodiment of a device in accordance with the invention for generating and delivering a fine mist for sterilizing or sanitizing.
Figure 3B:
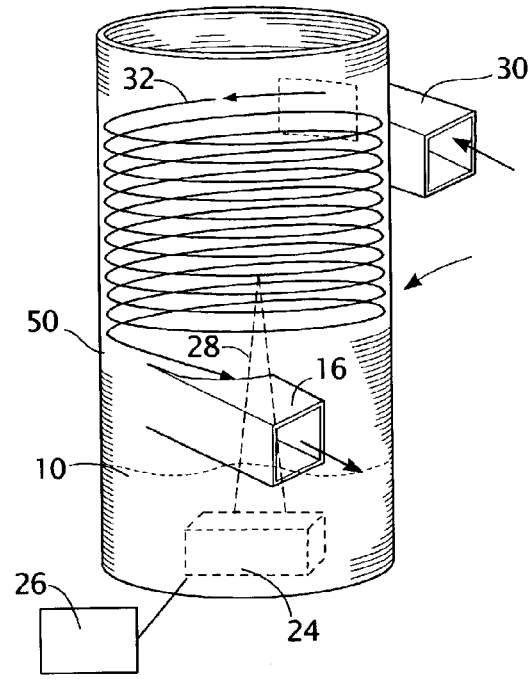
FIG. 3b is a perspective view of one embodiment of a device in accordance with the invention for generating and delivering a fine mist for sterilizing or sanitizing.
Figure 6:
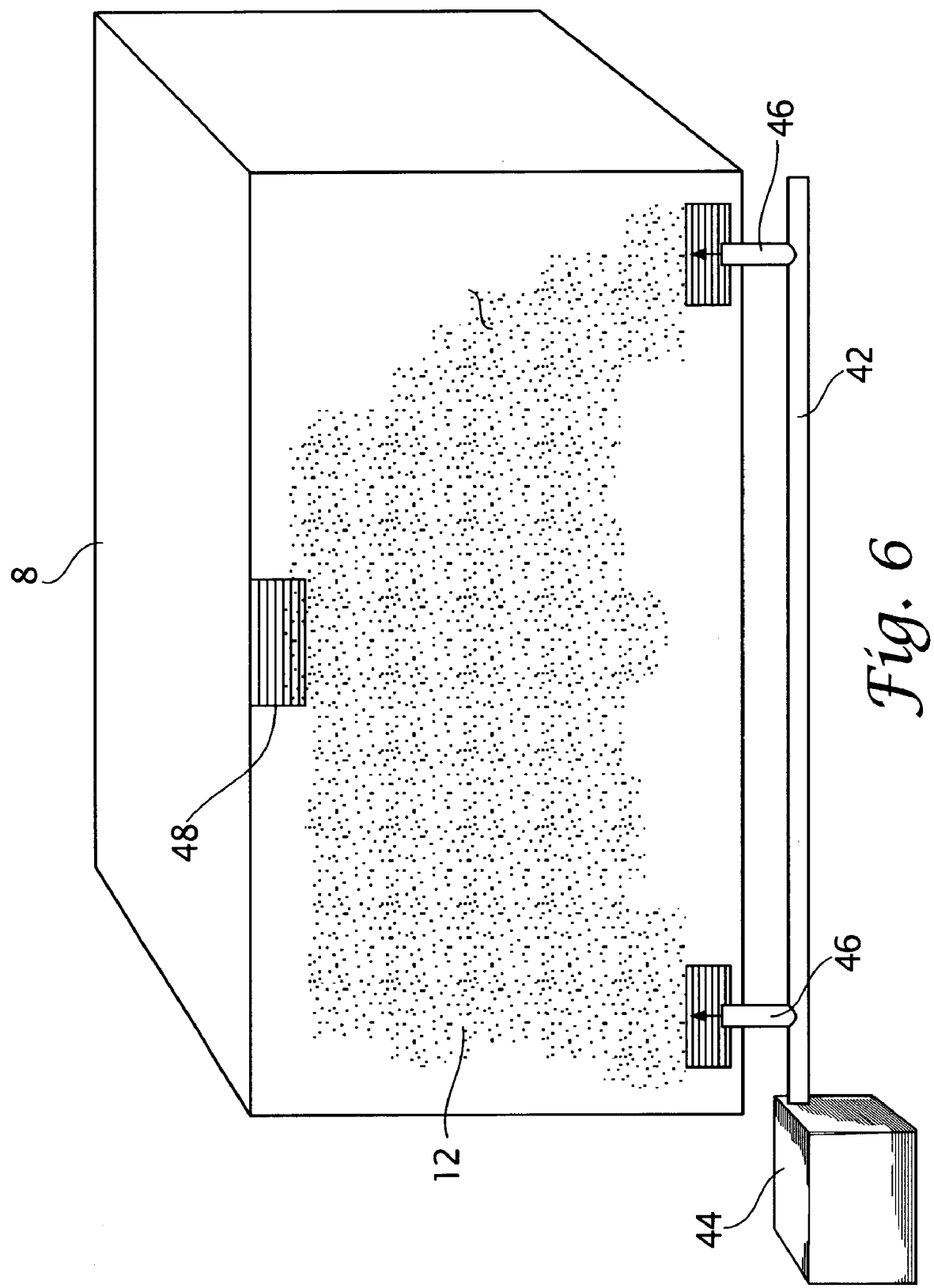
FIG. 6 is a schematic illustration of a second embodiment of the invention for the treatment of a volume of space using a fine-mist generating device.

In the embodiment shown in FIGS. 3a and 3b, rather than utilizing high-pressure systems or heat-based systems, the present invention provides for production of scalable throughput using a high frequency ultrasonic device. Heretofore, using high frequency ultrasonic devices has been considered impractical for the throughput levels desired of such a fine scale mist. Further, the fine scale mist previously could not be created and delivered in a stable manner in which mist droplets could remain stable and not coalesce prior to successful treatment of a site.

In the present invention, a controlled flow of carrier medium is provided to the generated mist to create a concentration of stable mist droplets within the carrier medium. The concentration of stable mist droplets may be scaled to an appropriate mass and delivered to a volume and its contents for treatment. The stable mist droplets are comprised of a biocide agent and companion substance or solvent molecules.

The biocide solution 10, preferably hydrogen peroxide solution, is subjected to ultrasonic waves driven by the piezoelectric transducer 24 to generate the mist at ambient pressure. No expensive technology is required to handle high pressure or heat based atomizing systems, so that the mist may be created cost effectively. The transducer provides the ultrasonic waves that atomize the solution to produce mist droplets, by converting an electrical frequency to mechanical vibrations. The mechanical vibrations of the piezoelectric device facilitate atomization of fluids by producing ultrasonic pressure or sound waves with rarefaction and compression cycles. The required high frequency pressure waves may be provided by localized cavitations using Q-switched laser device also. Above a certain limit, rarefaction produces cavitations resulting in bubbles, which expand during the negative pressure excursion and implode violently during the positive excursion. These cavitations cause the imploding bubbles to surface out as small droplets during compression and form a fog-like mist 12. Therefore, the ultrasonic waves produced by the high frequency vibration cause atomization of the solution into a cloud of particles or mist droplets. Alternative theories have been suggested to explain the atomization process when using ultrasonic waves and should be considered equally applicable to the present invention. Regardless of the theoretical cause atomization of a substance under the influence of ultrasonic waves, the droplet size produced by the atomization process depends upon the cube root of surface tension of the substance, the density of the substance, and the square of frequency of oscillation.

Typical transducers available commercially are used in medical applications, cleaning, and humidifying and operate with oscillating frequencies of 1.7 MHz to 2.4 MHz. These transducers produce 1 to 10 micron droplets of water mist. Depending on the desired mist quality and quantity of fine droplets, modifications in frequency or the mechanics of the piezoelectric transducer 24 may be made in accordance with the present invention for smaller droplet size and scalable output. A transducer may be varied in size of oscillating element to modify mist generation from the reservoir. Also, a transducer may accommodate frequency of mechanical oscillation of 20 MHz or more. And further, an array of piezoelectric oscillating elements may be arranged in combination to collectively form the transducer and provide an additional means of increasing the generation of mist 12. For instance, in one embodiment an array of 9 piezoelectric elements may be arranged in a 3 by 3 array. Increased mist generation volume may assist in the throughput of fine quality mist effective in sterilization using hydrogen peroxide solution 10. However, it should be noted that increased throughput of a fine scale mist as discussed herein would not be possible without further improvements as provided by the invention for extraction and delivery of the mist droplets.

The extraction method herein provides a device, as illustrated in embodiments in FIGS. 3a and 3b, for delivering very fine droplets of about 10 micron or less or nanoscale droplets less than one micron in diameter. The extraction method controls the flow of carrier medium to provide extraction of quality droplets in high quantities. The low kinetic energy created by the controlled momentum of the extraction method maintains droplet stability and inhibits coalescing of the droplets prior to effective treatment. The extraction method operates by removing the smaller droplets from the plume or column 28 of mist being generated by the high frequency ultrasonic oscillations. In particular, the smaller droplets are concentrated away from the center of the plume as shown in FIG. 4, while conversely the larger droplets are concentrated in the center. The present extraction method and device does not disrupt the center of the plume of mist as it is generated. Rather, a flow of carrier gas or air is provided flowing tangentially with respect to the plume. The tangential flow is directed to the outer portion of circumference of a circular cross section of the plume, such that the flow is directed tangentially at the mist fountain column at its entrance, as shown by the inlet 30, into the fountain column 28.

The outlet 16 and inlet 30 may be situated as shown in FIG. 3a with the inlet near the lower portion of the mist chamber 50. Alternatively, the arrangement may be switched as shown in FIG. 3b, and the inlet 30 may be situated near the upper portion of the chamber 50 with the outlet 16 preferably just above the level of the liquid reservoir. With the outlet near the surface level of the reservoir, the output of mist has been found to be more efficient, possibly because mist in general is heavier than air. Also, while the inlet 30 is preferably tangentially situated with respect to the chamber wall 50, the outlet 16 does not have to be tangentially situated to receive effective mist throughput. Regardless of the alternate arrangement of inlet 30 and outlet 16, the accomplishment of an efficient throughput of a quality fine mist by generating a strong flow near the column walls without disturbing the central plume and entraining larger undesirable droplets does not change. The flow behavior created by the arrangement taught by the invention optimizes and improves the extraction of fine mist droplets and maintains the usefulness of the cavitation process by preventing the disruption thereof during extraction of the mist droplets.

Because the smaller droplets are situated in the outer portion of the column 28, the tangential flow of carrier gas operates as a filter or classifier to separate the nanoscale droplets from the plume and carry them to the outlet of the device. The result of the tangential flow of carrier is a strong swirl of carrier gas flow 32 along the sides of the device 50 and away from the center of the column 28, but with very little flow of carrier gas in the center of the device or near the center of the column, which is illustrated in FIG. 4. The smaller droplets in the mist near the outer wall of the column are pulled into the swirling flow 32 along the outer wall of the column, and the larger droplets closer to the center of fountain plume remain and fall back into the reservoir bed of solution, as illustrated in FIG. 4. Thus, a mist having a high concentration of smaller droplets is produced that provides several advantages to the present invention.

Several such devices may be combined and connected to provide a series of chambers to increase the overall mist throughput. Thereby, a given inlet mass flow of carrier gas may be provided to a first chamber, and successive chambers may receive mist flow from the previous units. As additional fine mist droplets are gathered, the mist will proceed to an outlet or another successive unit. The chambers may be connected by conduits situated tangential to the chamber walls such that mist flow and carrier gas flow does not disturb the plume generated in each chamber. These devices may be modular and the number of devices to be in communication with each other may be varied at will. After dispersion the mist may be re-circulated back into the misting device upon meeting the mist's required log-time. The mist that coalesce and condenses may be introduced back into the reservoir of the misting device for re-misting. Alternatively, the biocide mist may be re-circulated in a volume to enhance the evenness in the mist's dispersion to the designated treatment site.

The smaller droplets comprising the mist 12 of biocide solution utilized for sterilization and the like in accordance with the invention will generally be less than ten microns or preferably nanoscale. The generation and extraction methods discussed make a high quality mist of extremely find droplets feasible. Such high quality mist may be produced by the present method at a throughput of up to 1 Lpm or more.

The mist 12, when comprised of extremely small droplets, characteristically performs as a pseudo gas-phase substance, as opposed to a liquid, vapor-phase, or gas-plasma substance, because the extremely small droplets exist in nearly molecular cluster state. Macroscopically the mist fluid looks like a gas phase substance that can barely be seen by human eye, while microscopically the mist fluid contains tiny droplets 34 in aqueous phase. The pseudo gas-phase characteristics of the mist fluid provides unique physical and chemical reactivity properties and behaves differently from either liquid or hot vapor phase with respect to its gas like flow and the stability of the hydrogen peroxide solution. Liquid phase hydrogen peroxide solution is easily obstructed and not practical for many applications considered for the invention, and vapor phase hydrogen peroxide solution is very unstable.

The ratio of mass flow rate of biocide agent mist to air may be varied to achieve a reasonable pseudo gas phase ppm (part per million) concentration of mist 12 for a specific treatment purpose. The mist expands more than 1000 to about 1500 times from its original liquid phase in a high quality mist of nanoscale droplet size. Further, the high production level of nanoscale droplets 34 supply a large increase in overall exposed surface area of mist droplets for a specific unit volume of liquid atomized. Combined the expanded mist and expanded surface area of droplets greatly enhance the effectiveness of the mist for treatment of bacteria and the like using a hydrogen peroxide solution mist.

Because water molecules surround the hydrogen peroxide molecules in the present mist droplets 34, the mist 12 of hydrogen peroxide solution 10 is very stable. Hydrogen peroxide produces H2O and nascent oxygen (reactive oxygen) when it decomposes. The nascent oxygen released from the hydrogen peroxide during decomposition is primarily responsible for the power of oxidizing organic matter, microorganisms, bacteria, or bacterial spores. The hydrogen peroxide in the mist remains stable without releasing nascent oxygen until the gas-like mist reaches the bacterial site or intended surface. The surrounding water molecules in the droplets prevent the decomposition of the hydrogen peroxide by preventing its contact with outside elements in the air during delivery. And, the surrounding water molecules delay the hydrogen peroxide vaporizing because the water molecules must vaporize first. Once the very small nanoscale droplets reach the intended target reaction site for disinfection, the small droplets provide a very reactive hydrogen peroxide mist solution.

The high reaction rates of the droplets 34 at the reaction sites for bacterial disinfection are due to several important features of the hydrogen peroxide mist 12 described herein. As discussed above, the small droplets cause the mist to have a very large surface area, and greater reactivity of the hydrogen peroxide mist results from the increase in exposed surface area of the reactive droplets. The increase in reactivity is relative to the increase in surface area.

In addition to increased overall surface area, for submicron scale droplets 34, the molecules of the water and hydrogen peroxide are concentrated on the surface of the droplets 34 in molecular clusters 36. FIG. 5 illustrates a submicron scale droplet 34 in accordance with a preferred embodiment of the invention. Molecules in the form of clusters tend to congregate on the surface 38 of the droplet 34. Meanwhile, the center 40 of droplet has relatively fewer number of molecules located there compared to surface. The effect of these surface concentrated molecular clusters is a very reactive droplet of biocide or hydrogen peroxide solution when very small submicron droplets are utilized, while large droplets are less reactive. The reactive hydrogen peroxide molecules located on the surface of the droplets simply provide for a more effective chemical reaction when the target molecules come into contact with the droplets. The surface concentrated hydrogen peroxide molecules will also react quickly with target molecules in the air, which is improves treatment of airborne bacteria and spores in fumigating a volume of space.

The present mist may be delivered to an area that is small and localized or very large, and the mist may be delivered in several manners. The mist may be used to totally flood an area for fumigation and sterilization. The mist may be used to partially flood an area for sanitization, and the mist may be used to spot treat an area in surface or volume applications.

The gas like flow of the mist provided by the invention enhances the effective delivery thereof and the collateral results. The mist is of such fine droplets that it is essentially dry and will not wet or damage materials in the area being treated, which is a signification advantage over chlorine dioxide and wet treatment methods. Delivery is effective because the mist acts as a pseudo gas, and its flow does not become obstructed by physical objects and barriers. As a result, the gas like mist can reach into crevices and corners due to its stability and unobstructed flow.

The mist generating and delivery device may be made to have a fixed throughput value according to the application. For example, a portable fumigating device, a bag-pack device, and a device for treating a large scale building may have a fixed throughput that is small, medium, and large, respectively, such that the mist is delivered at throughput rates of a few milliliters per minute to a few liters per minute, while retaining droplet size of less than a micron.

In one embodiment illustrated in FIG. 6, a mist may be generated and delivered through a transport pipe or tube 42 to a distant site without appreciable loss of mist throughput. This design provides the capability to centrally generate the mist in a predetermined generating location 44 and deliver it to the intended location or site 8 for sterilization. In particular, a high-throughput mist 12 generated in a truck or a stationary device 44 may be conveniently delivered to an air duct system 46 or the like for sterilization or sanitization via a transport pipe 42, such as a three-inch tube. In addition, the transportability and stability of the sterilizing mist 12 is advantageous in novel applications for cleaning the HVAC air ducts themselves of residential and commercial buildings. Because of allergy and bacterial infections often encountered at home and in office buildings, as well as the persistent problem of sick building syndrome, air duct cleaning is an important application of the mist sterilization methods presented herein.

Although liquid phase hydrogen peroxide concentration may be about 3% wt, the gas phase concentration will be different. The carrier gas or circulating airflow and blowers at the generating device introduce gas phase homogenization inside the room altering the parts per million level of hydrogen peroxide molecules. Throughput may be managed for treatment in commercial and larger applications such as rooms or buildings. The quality of mist and throughput available by the teachings herein are crucial for decontamination of rooms or buildings contaminated with bacterial spores such as encountered in 2001 in Hart Senate Building due to anthrax. Further, exposure may be varied in duration, as measured by how long generation of mist proceeds and throughput compared with volume of area treated. Similarly, the concentration of the hydrogen peroxide solution may be varied and offset by the duration of exposure, whereby one may use a longer exposure time and a lesser concentration of hydrogen peroxide solution. Residence time and vaporization rates such that mist remains stable for sufficient length of time for effective treatment should also be considered in devising the proper concentration and throughput of mist. Promoted by small droplet size and efficient delivery, the decomposition into reactive oxygen will provide the extreme chemical oxidation power of hydrogen peroxide as a sterilizing agent once the droplets reach the target.

The present device and method for fine mist sterilization may be used in sterilization, decontamination, sanitation, deodorization, and disinfection. Such may be applied to kill bacteria, bacterial spores, and microorganisms. The device and method described may be suitable for sterilization of localized small areas and items and sterilization of larger areas such as hospital rooms, office buildings, dwelling areas, and their contents. In addition, the device and method may be used in HVAC air duct cleaning.

Complete sterilization or partial sanitation may be the goal and may be achieved by varying concentration and exposure time of mist. And yet further, the device and method of hydrogen peroxide mist sterilization described may be combined with other forms of sterilization to enhance the power thereof or to accelerate sterilization and reduce the required exposure time of the hydrogen peroxide mist. Possible combinations and enhancements may include the addition of photo-sensitizer compounds, the coupling of the mist with UV radiation, or the combination of the solution with other agents for sterilizing or fumigating.

In one embodiment of a device of the invention, a unit for generating a mist 12 may be placed in a room 8 for sterilizing. The unit may generate a mist at a predetermined rate as determined by room volume and the density of spores or bacteria to be killed or inhibited. In another embodiment, mist throughput may be coupled to an HVAC outlet 46 to a room to flood the room 8 with mist 12. The room's vents 48 may then be closed to conserve the mist and reduce quality of mist required for sterilization. Similarly, the mist throughput could be provided to an HVAC system to treat and clean air ducts. Another application could involve a hand-held applicator that is portable and may be used for small areas, ceilings or for surface and spot sterilizing. Momentum jets may be incorporated into any such unit for directing the throughput. For such a small unit, a throughput of only 0.01 Lpm may be sufficient, but could be varied. On a slightly larger scale, a bag pack carrying kit, rolling cart or the like may be used for sanitizing. One example would be use by soldiers to sterilize tents or battlefield areas, or a dilute hydrogen peroxide mist could be applied to a person's clothing. In general, units operable in accordance with the invention may come in a variety of configurations and sizes with throughput values ranging from 0.005, 0.1 Lpm, 0.5 Lpm, 1 Lpm, to 10 Lpm.

In another embodiment, the device and method of the invention may be used in sterilizing one or more small surgical instruments or other items placed in a cabinet or container of relatively small volume compared to a room or building. By delivering to the container a hydrogen peroxide or biocide mist, these type items may be put inside a pouch or container where the hydrogen peroxide or biocide agent can effectively diffuse inside the container to sterilize or sanitize. The effectiveness of such a treatment would be enhanced by the nanoscale droplet size of the preferred quality mist generated.

It is expected that the present invention will permanently replace many existing chemical based sterilizing agents that are environmentally toxic in view of the nearly 100% killing rate of bacteria and unsanitary microorganisms when exposure time and concentration optimized. Advantages of the present device and method utilizing hydrogen peroxide as a biocide agent are significant. Hydrogen peroxide as an agent is environmentally friendly and any hydrogen peroxide gas escaping in leaks is not harmful since the products of decomposition are non-toxic. Hydrogen peroxide as an agent is also non-toxic to handle in low concentrations, has no adverse effects on occupants while treating a contaminated space, has no adverse bleaching effects on items and surrounding objectives, and does not leave any toxic residues requiring post treatment cleaning. Thus, the hydrogen peroxide fine mist device and method are capable of killing bacteria within a short time interval, less than one hour, without requiring excessive control of air leaks and excessive safety precautions, saving a tremendous amount of money over more toxic regimens currently available. Enhancing these advantages, the hydrogen peroxide solution may be used in relatively low concentrations, and hydrogen peroxide is relatively inexpensive and plentiful, making it a cost effective chemical for use in sterilization.

The hydrogen peroxide biocide can be coupled with additional sterilizing agents to further the purposes of the invention. For instance, hydrogen peroxide ($H_2O_2$) may be coupled with ozone (O3) to produce a more reactive and faster oxidation process using hydroxyl radical. Hydrogen peroxide and ozone react to produce the hydroxyl radical as follows:

$$H_2O_2+O_3 \rightarrow 2OH^*+3/2O_2 \rightarrow H_2O+2O_2$$

The combining of ozone and hydrogen peroxide would increase efficiency and the rate of oxidation by the conversion of ozone molecules to hydroxyl radicals and by the improved transfer of ozone from gas phase to liquid because of increases in ozone reaction rate caused by peroxone. The hydroxyl radical has a higher oxidation potential that O3, $H_2O_2$, Cl2 and MnO4. The hydroxyl radical is second only to fluorine in oxidation potential and results in more effective destruction of difficult to treat organic contaminants such as taste and odor compounds and halogenated compounds. Thus, in systems that require complete oxidation of taste and odor compounds or refractory organics, a combination of hydrogen peroxide and ozone might be beneficial. Hydrogen peroxide to ozone ratios are typically 0.4-0.5. This combination provide yet one possible variation of the method in the following claims for producing a high quality sterilizing mist of extremely fine droplets with throughput and stability sufficient for treatment of a volume of space such as a room and the contents thereof.

The present invention could also be used alone or in combinations for odor control, inorganic oxidation, organic oxidation, and bio-control. For a first example, in odor control, the biocide agent of the biocide mist may be used to oxidize hydrogen sulfide, mercaptans, amines and aldehydes. The biocide mist may be applied directly to wastes and aqueous wastes containing these odorants or to wet scrubbers used to remove them from airstreams. In a second example, in inorganic oxidation, the biocide mist may be used to oxidize cyanides, NOx, SOx, nitrites, hydrazine, carbonyl sulfide, other reduced sulfur compounds, and to reduce volatile organic compounds (VOC). In a third example, in organic oxidation, the biocide mist may be used to treat hydrolyzes formaldehyde, carbon disulfide, carbohydrates, organophosphorus and nitrogen compounds, and various water-soluble polymers. With catalysis, the biocide mist may be used in organic oxidation to destroy phenols, treat pesticides, solvents, plasticizers, chelants, and virtually any other organic requiring treatment. Finally, in a fourth example, in bio-control, the biocide mist may be used to restrain excess microbial growth in cooling circuits, and with catalysis to disinfect or to control growth of mold.

While the present invention has been particularly shown and described with reference to the embodiments thereof, it will be understood by those skilled in the art that various changes in form and detail may be made without departing from the spirit and scope of the present invention.

We claim:

1. A method for sterilizing, sanitizing, decontaminating or disinfecting including the steps of:
   a. providing an aqueous biocide solution;
   b. providing a high frequency wave generating device in communication with the aqueous biocide solution;
   c. generating a fountain column of mist droplets from the aqueous biocide solution using the high frequency wave generating device;
   d. directing a carrier medium tangential to the fountain column;
   e. entraining mist droplets into the carrier medium to create a biocide mist for delivery to a treatment site; and
   f. delivering the biocide mist to a treatment site for sterilizing, sanitizing, decontaminating, or disinfecting the treatment site.

2. A method of sterilizing, sanitizing, decontaminating or disinfecting as in claim 1 in which the aqueous biocide solution is includes hydrogen peroxide.

3. A method of sterilizing, sanitizing, decontaminating or disinfecting as in claim 2 in which the aqueous biocide solution includes less than 10% by weight hydrogen peroxide in water.

4. A method of sterilizing, sanitizing, decontaminating or disinfecting as in claim 2 in which the aqueous biocide solution includes about 3% by weight hydrogen peroxide in water.

5. A method of sterilizing, sanitizing, decontaminating or disinfecting as in claim 1 in which the high frequency wave generating device is a piezoelectric transducer.

6. A method of sterilizing, sanitizing, decontaminating or disinfecting as in claim 1 in which the high frequency wave generating device is arranged in communication with the aqueous biocide solution by submerging the high frequency wave generating device in the aqueous biocide solution.

7. A method of sterilizing, sanitizing, decontaminating or disinfecting as in claim 1 in which the carrier medium is directed tangential to the fountain column using an inlet situated tangential to the fountain column of mist droplets.

8. A method of sterilizing, sanitizing, decontaminating or disinfecting as in claim 1 in which the step of generating the fountain column of mist droplets from the aqueous biocide solution using the high frequency wave generating device is accomplished at ambient temperature and ambient pressure.

9. A method of sterilizing, sanitizing, decontaminating or disinfecting as in claim 1 in which the fountain column of mist droplets includes a peripheral portion and a central portion, and during the step of entraining mist droplets into the carrier medium to create a biocide mist for delivery to a treatment site, the carrier medium causes a strong swirl flow to be created in the peripheral portion and the central portion is not significantly disturbed by the carrier medium or a weaker swirl flow is created in the central portion.

10. A method of sterilizing, sanitizing, decontaminating or disinfecting as in claim 1 in which the step of delivering the biocide mist to a treatment site for sterilizing, sanitizing, decontaminating, or disinfecting the treatment site includes directing the biocide mist into a room area and providing sufficient throughput for elimination of contaminants in the room area.

11. A method of sterilizing, sanitizing, decontaminating or disinfecting as in claim 1 in which the step of delivering the biocide mist to a treatment site for sterilizing, sanitizing, decontaminating, or disinfecting the treatment site includes directing the biocide mist into a air duct system and providing sufficient throughput for elimination of contaminants in the air duct system.

12. A method of sterilizing, sanitizing, decontaminating or disinfecting as in claim 9 in which said biocide mist is comprised of hydrogen peroxide solution.

13. A method of sterilizing, sanitizing, decontaminating or disinfecting as in claim 1 in which a greater part of the mist droplets forming the biocide mist have a droplet diameter of less than ten micron.

14. A method of sterilizing, sanitizing, decontaminating or disinfecting as in claim 1 in which a greater part of the mist droplets forming the biocide mist have a droplet diameter of less than one micron.

15. A method of sterilizing, sanitizing, decontaminating or disinfecting as in claim 1 including the step of adjusting frequency and mechanical arrangement of the high frequency wave generating device for generating the fountain column of mist droplets to vary quality and quantity of the mist droplets produced.

16. A method of sterilizing, sanitizing, decontaminating or disinfecting comprising the steps of:
   a. providing an aqueous biocide solution comprised of a biocide and solvent;
   b. providing a high frequency pressure wave to interact with a reservoir containing the aqueous solution and producing a biocide mist that flows from a fountain plume created by the providing of the high frequency pressure wave to the reservoir containing the aqueous biocide solution, the biocide mist having a proportion of sub-micron diameter droplets comprised of the biocide and solvent from the biocide solution and being stabilized by surrounding molecules of the biocide by molecules of water within the droplets;
   c. introducing the biocide mist to a flow of carrier medium to create a mass of the biocide mist and carrier medium having a sufficient concentration of the biocide mist to effectively treat the treatment site or the contained volume of space and the flow of carrier medium is tangential to the fountain plume so as not to significantly disturb the fountain plume; and
   d. introducing the biocide mist to a treatment site or contained volume of space.

17. A method of sterilizing, sanitizing, decontaminating or disinfecting comprising the steps of:
   a. providing an aqueous biocide solution comprised of a biocide and solvent in which the aqueous biocide solution is corrosive and the aqueous biocide solution is situated within a chemically resistant container;
   b. placing the chemically resistant container in communication with an external medium, and transferring the ultrasonic vibrations from the external medium to the aqueous biocide solution via the communication of the chemically resistant container with the external medium and producing a biocide mist having a proportion of submicron diameter droplets comprised of the biocide and the solvent from the biocide solution and being stabilized by surrounding the molecules of the biocide by the molecules of water within the droplets; and
   c. introducing the biocide mist to a treatment site or contained volume of space.

18. A method of sterilizing, sanitizing, decontaminating or disinfecting as in claim 17 in which the external medium is a water-bed.

* * * * *